United States Patent
Chen et al.

(10) Patent No.: US 8,673,216 B2
(45) Date of Patent: Mar. 18, 2014

(54) DETECTION OF TRACE CHEMICALS AND METHOD THEREFOR

(75) Inventors: Antao Chen, Lake Forest Park, WA (US); Danling Wang, Seattle, WA (US); Qifeng Zhang, Seattle, WA (US); Guozhong Cao, Seattle, WA (US)

(73) Assignee: The University of Washington, Seattle, WA (US)

( * ) Notice: Subject to any disclaimer, the term of this patent is extended or adjusted under 35 U.S.C. 154(b) by 0 days.

(21) Appl. No.: 12/960,341

(22) Filed: Dec. 3, 2010

(65) Prior Publication Data

US 2011/0151574 A1 Jun. 23, 2011

Related U.S. Application Data

(63) Continuation of application No. PCT/US2009/046157, filed on Jun. 3, 2009.

(60) Provisional application No. 61/058,525, filed on Jun. 3, 2008.

(51) Int. Cl.
*G01N 27/00* (2006.01)

(52) U.S. Cl.
USPC ....... 422/82.02; 422/50; 422/82.01; 436/149; 73/31.06; 257/210

(58) Field of Classification Search
None
See application file for complete search history.

(56) References Cited

U.S. PATENT DOCUMENTS

| | | | |
|---|---|---|---|
| 5,138,889 A | 8/1992 | Conrad | |
| 7,189,353 B2 | 3/2007 | Lewis | |
| 8,052,932 B2 * | 11/2011 | Han et al. | 422/90 |
| 2006/0000259 A1 | 1/2006 | Rothschild | |
| 2006/0231420 A1 | 10/2006 | Garzon | |
| 2007/0261959 A1 * | 11/2007 | Kim et al. | 204/424 |
| 2008/0006078 A1 | 1/2008 | Chueh | |
| 2008/0116490 A1 | 5/2008 | Stewart | |

FOREIGN PATENT DOCUMENTS

JP 7209235 A 8/1995

OTHER PUBLICATIONS

Varghese, O. K. et al., Extreme changes in the electrical resistance of titania nanotubes with hydrogen exposure, 2003, Advanced Material, vol. 15(7-8), pp. 624-627.*
Berven, C., et al. Nanowire-nanoparticle gas sensors, PNACP, Apr. 11, 2008.*
International Search Report and Written Opinion mailed Mar. 19, 2010, issued in corresponding International Application No. PCT/US2009/0446157, filed Jun. 3, 2009, 6 pages.
Filanovsky, B., et al., "Carbon Electrodes Modified With $TiO_2$/Metal Nanoparticles and Their Application to the Detection of Trinitrotoluene," Advanced Functional Materials 9(17)1487-1492, Jun. 2007.
Francioso, L., et al., "$TiO_2$ Nanowires Array Fabrication and Gas Sensing Properties," Sensors and Actuators B: Chemical 130(1):70-76, Mar. 2008.

(Continued)

*Primary Examiner* — Robert Xu
(74) *Attorney, Agent, or Firm* — Christensen O'Connor Johnson Kindness PLLC

(57) ABSTRACT

The invention provides devices, systems, and methods for detecting an analyte vapor. Particularly, electronegative analyte vapors, such as those vapors evolving from explosive compounds, are typical analytes detected the devices. The devices operate using a resistivity change mechanism wherein a nanostructured chemiresistive material undergoes a resistivity change in the presence of an analyte vapor. A resistivity change indicates the presence of an analyte.

12 Claims, 8 Drawing Sheets

(56) References Cited

OTHER PUBLICATIONS

Han, L., et al., "Nanoparticle-Structured Sensing Array Materials and Pattern Recognition for VOC Detection," Sensors and Actuators B: Chemical 106(1):431-441, Apr. 2005.

Kim, I.-D., et al., "Ultrasensitive Chemiresistors Based on Electrospun $TiO_2$ Nanofibers," Nano Letters 6(9)2009-2013, Sep. 2006.

Extended European Search Report mailed Jul. 22, 2013, issued in corresponding Application No. EP 09 808 549.1, filed Jun. 3, 2009, 6 pages.

* cited by examiner

DETECTION OF TRACE CHEMICALS AND METHOD THEREFOR

CROSS-REFERENCES TO RELATED APPLICATIONS

This application is a continuation of International Application No. PCT/US2009/046157, filed Jun. 3, 2009, which claims the benefit of U.S. Provisional Application No. 61/058,525, filed Jun. 3, 2008, the entire disclosures of which are incorporated herein by reference.

STATEMENT OF GOVERNMENT LICENSE RIGHTS

This invention was made with Government support under Grant No. N00014-05-1-0843 awarded by Office of Naval Research. The Government has certain rights in the invention.

BACKGROUND

The detection of highly explosive compounds, such as those used in land mines, is a necessity for modern warfare and counterterrorism. Sensing such explosives is a difficult task due to the low vapor pressure of common explosive materials, such as trinitrotoluene (TNT) and related nitroaromatic explosives, which typically have a vapor pressure in the parts per million (ppm) range or lower.

Many explosives detectors currently available, such as ion mobility spectrometers used in airports, are not portable. Sensors based on fluorescence quenching are field-deployable, but are relatively bulky and consume large amounts of power, thus making the devices hand-held portability questionable. Fluorescence-quenching sensors additionally have the detraction of photo-degradation issues of the organic sensing materials used.

With the current worldwide emphasis on counterterrorism and homeland security, an inexpensive, portable, and highly sensitive explosives detector is urgently needed to provide the necessary capabilities for eliminating the substantial threat to human life posed by such explosives.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, a device for detecting an electronegative analyte vapor is provided, comprising: a film comprising a nanostructured chemiresistive material having a first resistivity in the absence of an electronegative analyte vapor and a second resistivity, different than the first resistivity, after exposure to the electronegative analyte vapor; and a resistivity-measuring device sized and configured to determine a resistivity of the film.

In another aspect, a system for detecting an electronegative analyte vapor in a vapor sample is provided, comprising: a first film comprising a first nanostructured chemiresistive material, wherein the first film has a first resistivity without exposure to an electronegative analyte vapor and a second resistivity, different than the first resistivity, after exposure to the electronegative analyte vapor; a first resistivity measuring device sized and configured to determine a resistivity of the first film; and a first vapor sample delivery device sized and configured to deliver a vapor sample to the first film.

In another aspect, a method for detecting an analyte vapor in a vapor sample is provided, comprising: determining the resistivity of a first film portion after exposure to a vapor sample, the first film portion comprising a nanostructured chemiresistive material, wherein the first film portion has a first resistivity without exposure to an analyte vapor and a second resistivity, different than the first resistivity, after exposure to the analyte vapor, wherein the analyte vapor changes the resistivity of the nanostructured chemiresistive material on contact; and comparing the resistivity of the first film portion after exposure to the vapor sample to a resistivity of the first film portion without exposure to the vapor sample to provide a first input for detecting the analyte.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1A:
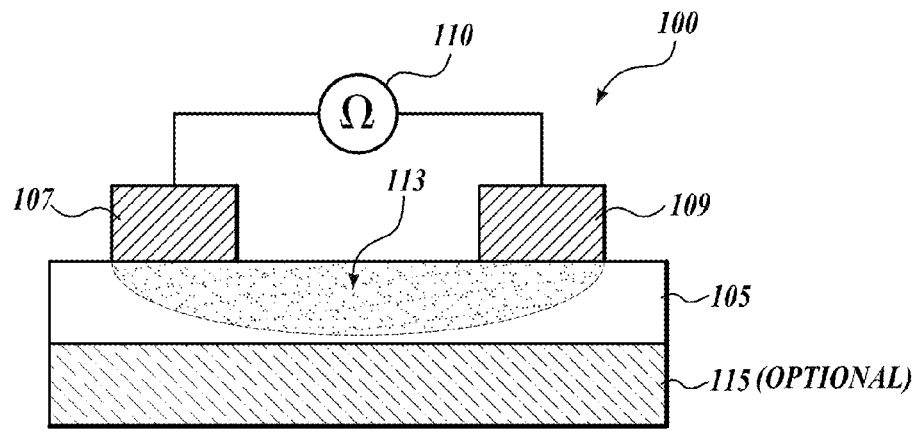
FIG. 1A is a diagrammatic cross-sectional view of a representative explosives sensing device of the invention.

While illustrative embodiments have been illustrated and described, it will be appreciated that various changes can be made therein without departing from the spirit and scope of the invention.

The invention provides devices, systems, and methods for detecting an analyte vapor. Electronegative analyte vapors, such as those vapors evolving from explosive compounds, are typical analytes detected by the devices. The devices operate using a resistivity-change mechanism by which a nanostructured chemiresistive material undergoes a resistivity change in the presence of an analyte vapor. A resistivity change indicates the presence of an analyte.

The invention also provides systems that include multiple devices utilized to provide multiple sensing inputs for a single analyte whereby each sensor has a unique response to the analyte. The combined inputs of multiple sensors yields a "fingerprint" for the particular analyte comprised of the individual responses of the sensors to the analyte.

In one aspect, a device for detecting an electronegative analyte vapor is provided, comprising: a film comprising a nanostructured chemiresistive material having a first resistivity in the absence of an electronegative analyte vapor and a second resistivity, different than the first resistivity, after exposure to the electronegative analyte vapor; and a resistivity-measuring device sized and configured to determine a resistivity of the film.

In another aspect, a system for detecting an electronegative analyte vapor in a vapor sample is provided, comprising: a first film comprising a first nanostructured chemiresistive material, wherein the first film has a first resistivity without exposure to an electronegative analyte vapor and a second resistivity, different than the first resistivity, after exposure to the electronegative analyte vapor; a first resistivity measuring device sized and configured to determine a resistivity of the first film; and a first vapor sample delivery device sized and configured to deliver a vapor sample to the first film.

In another aspect, a method for detecting an analyte vapor in a vapor sample is provided, comprising: determining the resistivity of a first film portion after exposure to a vapor sample, the first film portion comprising a nanostructured chemiresistive material, wherein the first film portion has a first resistivity without exposure to an analyte vapor and a second resistivity, different than the first resistivity, after exposure to the analyte vapor, wherein the analyte vapor changes the resistivity of the nanostructured chemiresistive material on contact; and comparing the resistivity of the first film portion after exposure to the vapor sample to a resistivity of the first film portion without exposure to the vapor sample to provide a first input for detecting the analyte.

The device is useful for detecting an electronegative analyte vapor. As used herein, the term "electronegative" refers to an analyte compound having a sufficient electronegativity to cause a measurable change in resistivity of the nanostructured chemiresistive material of the device upon contact. Typical electronegative analyte vapors include vapors of explosive compounds. Explosive vapors of explosive materials typically having low vapor pressures, for example, 1 ppm or lower.

Representative explosive compounds that can be detected by the devices and systems of the invention include trinitrotoluene (TNT), dinitrotoluene (DNT), cyclotetramethylenetetranitramine (HMX), cyclotrimethylenetrinitramine (RDX), 2,4,6-trinitrophenol (PA), methyl-2,4,6-trinitrophenylnitramine (tetryl), pentaerythritol-tetranitrate (PETN), silicon-PETN, nitroglycerine, and mixtures thereof.

Typical explosives detectable with the device include nitroaromatic explosives, such as DNT and TNT. Additionally, non-aromatic nitro-containing explosives are detectable with the device, including PETN, Si-PETN, and nitroglycerine.

Electronegative analyte vapors from explosives are difficult to detect using known techniques, not only because of the low vapor pressure of the compounds—and, thus, small analyte population—but also because of the electronegativity of the analytes. The high electronegativity of the analyte compounds causes strong adhesion of the molecules to surfaces, complicating sensing mechanisms and creating unwanted buildup of analyte on surfaces of detection devices (e.g., chromatographic devices). While such adsorption is considered an unwanted complication for sensing of electronegative explosive analytes with known detection devices, adsorption is beneficial in the present invention because it provides for a strong interaction between the nanostructured chemiresistive materials of the device and the analyte. A stronger chemiresistive effect and more sensitive detection of the analyte results.

The devices of the invention utilize a nanostructured chemiresistive material that changes resistivity upon exposure to the electronegative analyte vapor. As used herein, the term "nanostructured" refers to materials having at least one physical dimension of about 500 nanometers or smaller. The nanostructured materials may include physical dimensions greater than about 500 nm if at least one physical dimension is less than about 500 nm. For example, in an exemplary embodiment, the nanostructured material is a film of nanowires having a width of about 100 nm and a length of about 2 microns.

The nanostructured material provides a large surface area for sensing analytes. Representative nanostructured materials include nanowires, nanotubes, nanoparticles, and mixtures thereof. Nanostructured materials can be formed in several conformations from the same material. For example, titanium dioxide nanowires can be formed in monoclinic, triclinic, and various other conformations, each having particular molecular geometry. Titanium dioxide can also be formed as nanoparticles. In one embodiment, the nanostructured chemiresistive material is a film of monoclinic titanium dioxide nanowires.

As used herein, the term "chemiresistive" refers to a physical effect in which the resistivity of a material is changed in response to a compound contacting the material. The change in resistance of the nanostructured chemiresistive material is typically caused by surface depletion of charge carriers in the material. Particularly, for example, n-type semiconductors are electron-rich materials that will form a charge-transfer complex upon contact with a highly electronegative compound (such as TNT). Upon contact between the electronegative analyte molecule and an n-type semiconductor, charge-carrier surface traps are created in the n-type semiconductor, which leads to a charge-carrier depletion region. The depletion of charge carriers results in an n-type semiconductor with decreased electrical conductivity, and thus increased electrical resistance.

In a representative embodiment, the nanostructured chemiresistive material includes n-type semiconductor nanowires, such as wires made of titanium dioxide. N-type semiconductors are useful in the devices of the invention because their electrical properties result in the depletion of surface charges upon adsorption of electronegative materials to their surface. Representative n-type semiconductors include titanium dioxide, zinc dioxide, and n-type silicon.

The nanostructure chemiresistive material is typically formed into a film, which is optionally supported on a substrate. The film is then exposed to the electronegative analyte vapor and the adsorption of the vapor onto the nanostructured chemiresistive material produces a detectable change in the resistivity of the film.

A resistivity-measuring device is included in the device of the invention. Resistivity measurements are known to those of skill in the art. It will be appreciated that any method for determining resistivity of the sensing region is useful in the invention, including optical and electronic methods. In one embodiment of the invention, electrical measurement of resistivity is utilized. In an exemplary embodiment, two electrodes are in contact with the surface of the nano structured chemiresistive material and the resistance of the film between the two electrodes is measured. In the method of the invention, the resistivity of the film is measured prior to exposure of the film to the analyte and then after exposure of the film to the analyte. The difference in the resistivities is the measured response of the device to the analyte. In an alternative embodiment, optical methods are used to characterize the surface depletion of charge carriers as an alternative to electrical resistivity measurements.

In one embodiment, the device includes a first electrode and a second electrode, separated by a sensing region of the nanostructured chemiresistive material. The sensing region is a region of the material that has its resistivity probed by the electrodes when resistivity measurements are performed.

A representative device of the invention is illustrated in FIG. 1A as a diagrammatic cross-sectional view. The device 100 includes a nanostructured chemiresistive material film 105 having a first electrode 107 and a second electrode 109 on its surface. A resistivity-measuring device 110 is symbolically illustrated in electrical communication with the first and second electrodes 107 and 109. The sensing region 113 is diagrammatically represented as the region that is probed by the resistive measurement of the device, and, thus, the region that produces the sensing effect of the device. It will be appreciated that the shape of the sensing region 113 in FIG. 1A is depicted for illustrative purposes only and may not be an accurate representation of the shape and size of an actual sensing region of a device of the invention. An optional substrate 115 can support the nanostructured chemiresistive material film 105.

A substrate 115 is particularly useful when forming devices of the invention as a platform upon which nanostructured chemiresistive materials can be deposited. For example, nanowires of titanium dioxide can be suspended in an organic solvent and spin cast onto a substrate to form a nanostructured chemiresistive material film. Spin coating, drop coating, or other liquid-based deposition techniques can be used in such an exemplary fabrication method. Upon evaporation of the organic solvent, the nanostructured chemiresistive material film is solidified, and electrodes 107 and 109 can then be deposited to complete the device.

Additional representative deposition methods useful for forming the nanostructured chemiresistive material film 105 include vapor deposition and solid-state deposition (e.g., thermal growth of nanowires from nanoparticles) methods, anodic oxidation, template processing, vapor-liquid-solid synthesis, solution phase synthesis, pulsed laser deposition, and other methods known to those of skill in the art.

Figure 1B:
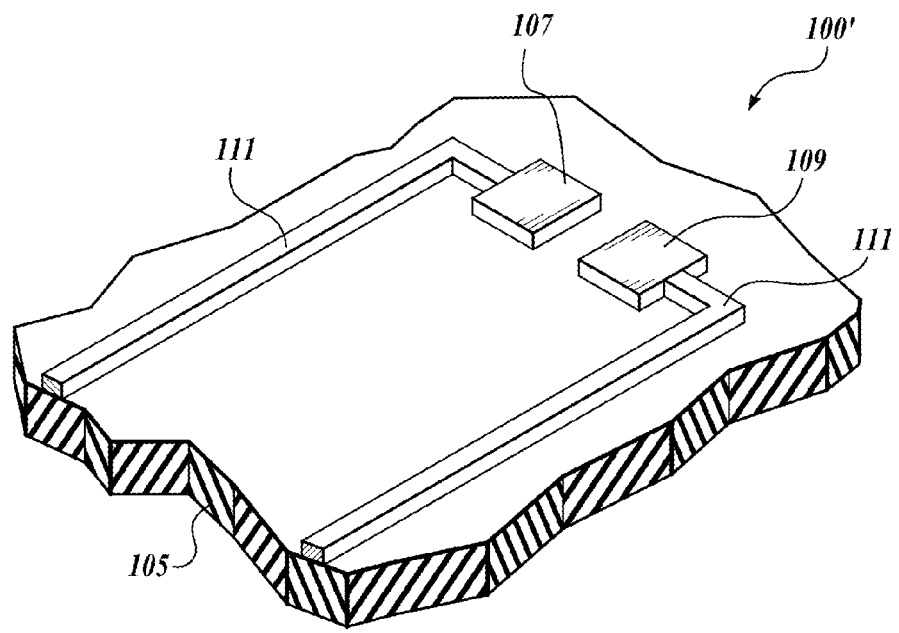
FIG. 1B is a prospective view of a representative explosives sensing device of the invention.

FIG. 1B is a perspective view of a portion of a representative device 100' of the invention that includes a nanostructured chemiresistive material 105 (with no substrate) upon which is deposited a first electrode 107, a second electrode 109, and traces 111 leading from the electrodes to a device for measuring the resistivity between the electrodes (not shown).

Figure 2:
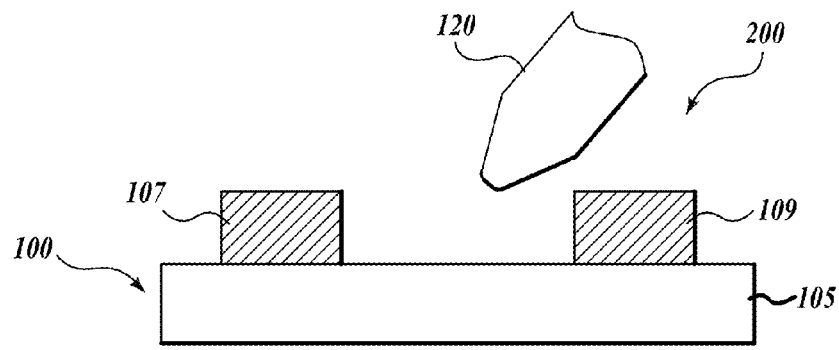
FIG. 2 is a diagrammatic illustration of a representative system for detecting explosive vapor in accordance with the present invention.

A representative system of the invention is illustrated in FIG. 2 that includes a device similar to that of FIG. 1A, including a nanostructured chemiresistive material film 105 and first and second electrodes 107 and 109 disposed thereon. The system 200 also includes an analyte delivery device 120 sized and configured to deliver an analyte vapor to the nanostructured chemiresistive material 105. Upon exposure to the analyte, the resistivity of the material 105 is measured between the first electrode 107 and second electrode 109.

A representative analyte delivery device 120 is a concentrator that samples a particular volume of gas and directs the gas toward the device 100. Such an analyte delivery device 120 is useful for sampling a large volume of gas and delivering that gas to a particular point on the device 100 such that any analyte within the (larger) sampled volume will be delivered to the device 100.

The analyte delivery device 120 is not necessary for the operation of a device of the invention (e.g., 100, 100') because ambient gas may be sampled. If the device is placed in close proximity to a source for the analyte, no analyte delivery device 120 would be needed. For example, if the device is brought into close proximity to a TNT land mine, an analyte delivery device 120 may not be necessary because the TNT vapors from the land mine would likely be present in the air around the device and would adsorb to the nanostructured chemiresistive material film 105 without the assistance of an analyte delivery device 120.

Figure 3:
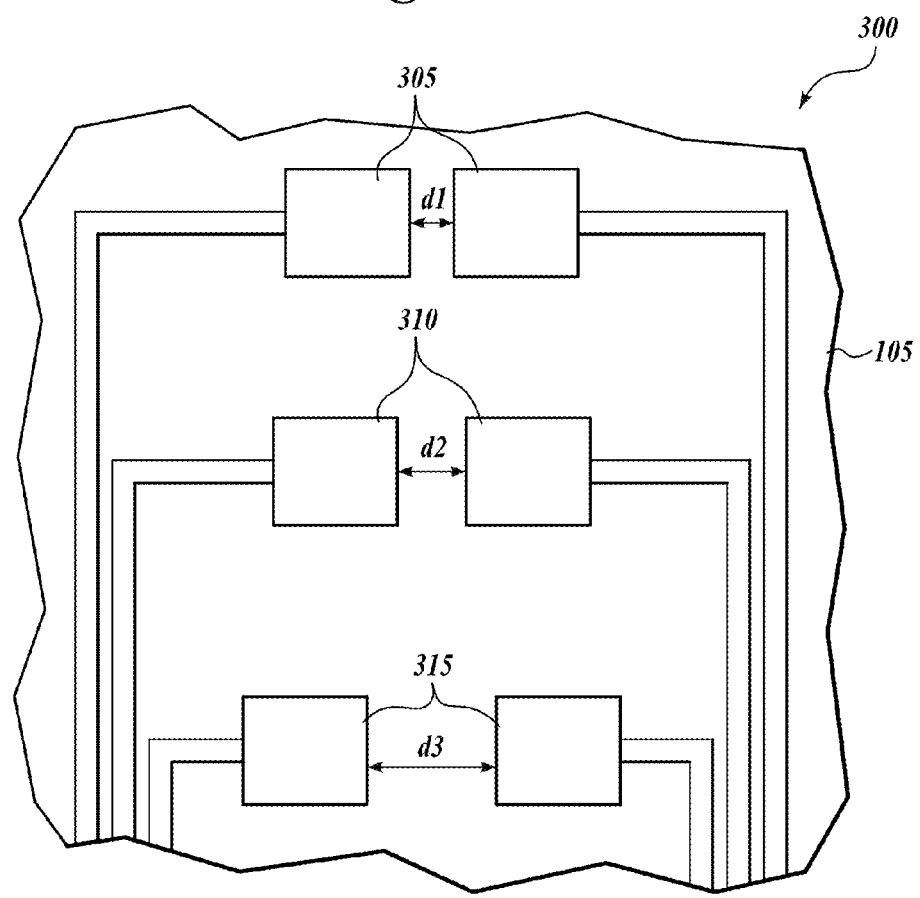
FIG. 3 is a plan-view illustration of a representative multi-sensor embodiment of the present invention.

The invention also provides devices having multiple sets of resistivity determining devices, such as electrodes. As illustrated in FIG. 3, a portion of a representative device 300 of the invention is illustrated that includes a nanostructured chemiresistive material film 105, a first electrode pair 305 having a first separation distance ($d_1$), a second electrode pair 310 having a second separation distance ($d_2$), and a third electrode pair 315 having a third separation distance ($d_3$), with the spacing between the electrodes in the three pairs increasing from the first pair 305 ($d_1$) to the second pair 310 ($d_2$), to the third pair 315 ($d_3$). The result of the varied spacing between the electrode pairs is a different resistivity measured between each electrode pair when the analyte vapor is exposed to the device 300. Because the spacing between the electrodes differs, a different response will be generated by each pair, and such differentiated responses can lead to multiple characterizations of the analyte. In one embodiment, the device includes a first electrode pair having a first separation distance and a second electrode pair having a second separation distance. In one embodiment, the first separation distance and the second separation distance are different.

Furthermore, an analyte can be characterized for later identification by using multiple devices of varying composition of the nanostructured chemiresistive material between the electrodes. For example, surface treatments, such as self-assembled monolayers (SAMs), can be used to chemically modify the surface of the film 105 such that two regions of the film 105 modified by two different self-assembled monolayers will produce different chemiresistive effects. By measuring the resistivity of the different portions of the film, an additional degree of characterization data of the response of the device to a particular analyte can be acquired. In one embodiment, the device includes a first surface treatment and a second surface treatment. In one embodiment, the first surface treatment and the second surface treatment are different.

As characterization of an analyte includes more reference data inputs, such as multiple electrode spacings and/or functionalization treatments (e.g., SAMs), the response of the device to a particular analyte can be determined. The combined measured responses of each different device to an analyte will provide a single "fingerprint" of the analyte. The analyte may subsequently be detected in a sample of unknown composition based on matching the response of the device to a fingerprint library of results derived from known analytes.

Surface functionalization of the nanostructured chemiresistive material is useful for the development of highly specific and sensitive devices. One benefit of utilizing a surface functionalization is improving sensor response by reducing nonspecific adsorption of interfering vapors in an ambient environment. Such vapors may crowd out the analyte vapors or provide false positive readings. Selectivity is typically achieved by introducing a chemical functionality onto the nanostructured chemiresistive material such that the material selectively interacts with the analyte vapor.

For example, many common explosive compounds contain nitro groups. Modifying a surface using a monolayer containing moieties capable of hydrogen bonding with nitro groups (e.g., hexafluoroisopropanol (HFIP)) creates preferential adsorption of nitro-containing analyte vapors onto a surface modified the monolayer. Thus, by applying a monolayer of a compound such as HFIP to the nanostructured chemiresistive material, additional selectivity for nitro-containing explosive analyte vapors can be achieved.

Additionally, nitroaromatic explosives, such as TNT, are known to form charge transfer complexes with electron-rich aromatic compounds, such as N,N,N',N'-tetramethyl-p-phenylenediamine (TMPD). The application of a monolayer of TMPD to the nanostructured chemiresistive material preferentially adsorbs aromatic explosives for increased sensitivity.

The above two paragraphs describe two particular schemes for utilizing surface functionalization of the nanostructured chemiresistive material to improve sensitivity and selectivity based on the characteristics of the analyte. It will be appreciated by those of skill in the art that additional sensitization and selectivity schemes can be integrated into the devices based on the properties of the analyte.

In one embodiment, the device includes a nanostructured chemiresistive material having more than one type of nanostructured chemiresistive material. In one embodiment, the nanostructured chemiresistive material film is comprised of nanowires and nanoparticles. In one embodiment, the device includes a nanostructured chemiresistive film of titanium dioxide nanowires and gold nanoparticles. In this exemplary embodiment, the addition of gold nanoparticles provides the titanium dioxide film with additional charge conduction mechanisms and an altered conduction path for resistivity measurements. The addition of nanoparticles to a nanowire film can enhance the sensitivity and response time of a device and also can be used in multiple-sensor devices to provide an additional input to characterize and identify a particular analyte.

The Formation of Titanium Dioxide Films for Devices of the Invention

As described above, titanium dioxide is a nanostructured chemiresistive material useful in devices of the invention. In an exemplary embodiment, the titanium dioxide is monoclinic titanium dioxide ($TiO_2$—B) formed as nanowires, which can be synthesized according to techniques known to those of skill in the art (typical reactants include $TiO_2$ nanoparticles in sodium hydroxide solution whereby nanowires are grown through a hydrothermal technique). The length and diameter of the $TiO_2$—B nanowires can be controlled through reaction conditions and ultrasonic treatment of the reactants.

In an exemplary embodiment, titanium dioxide nanowires are formed using the following experimental procedure. Titania nano-particle powder (commercially available) was mixed with 10M NaOH and reacted in an autoclave at 180° C for 36 hours. The as-obtained TiO2-B nanowire precipitate was rinsed with 0.1M HCl utill the pH value reached ~5, and then washed with DI-water. TiO2-B nanowires fabricated through this procedure have an average diameter of about 20 nm and a length up to several micrometers.

Representative Device Fabrication

Figure 4:
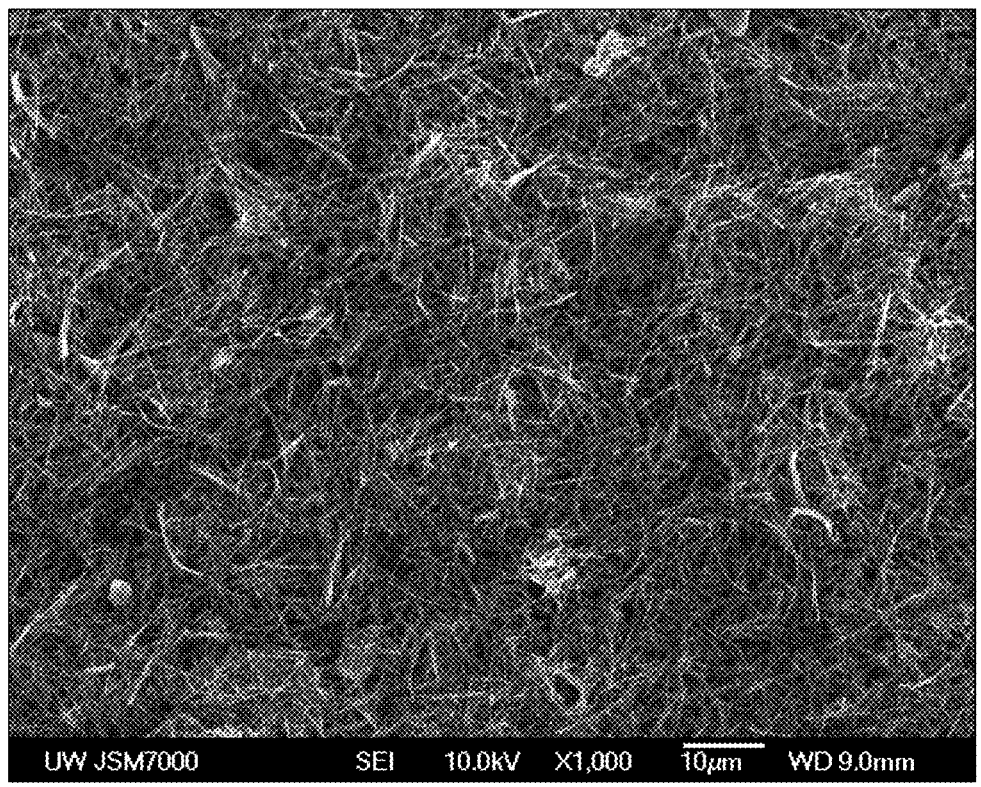
FIG. 4 is a scanning electron micrograph of a nanostructured chemiresistive material useful in the present invention.

In an exemplary embodiment, a device of the invention incorporating $TiO_2$—B nanowires is fabricated by first suspending the nanowires in an organic solvent, such as ethanol, drop coating the suspension on a glass substrate, and drying in an oven at 70° C. to form a thin film of $TiO_2$—B nanowires several micrometers thick. Microscopically, the nanowire film is a 3-dimensional mesh randomly oriented and interconnected nanowires, as pictured in the scanning electron micrograph of FIG. 4. The device fabrication proceeds by depositing metal electrodes, such as aluminum, gold, copper, or silver. In an exemplary embodiment, the electrodes are circular in shape, 4 mm in diameter, and spaced 1 cm apart (edge-to-edge distance).

Resistivity Testing of Vapors from Explosives

Figure 5A:
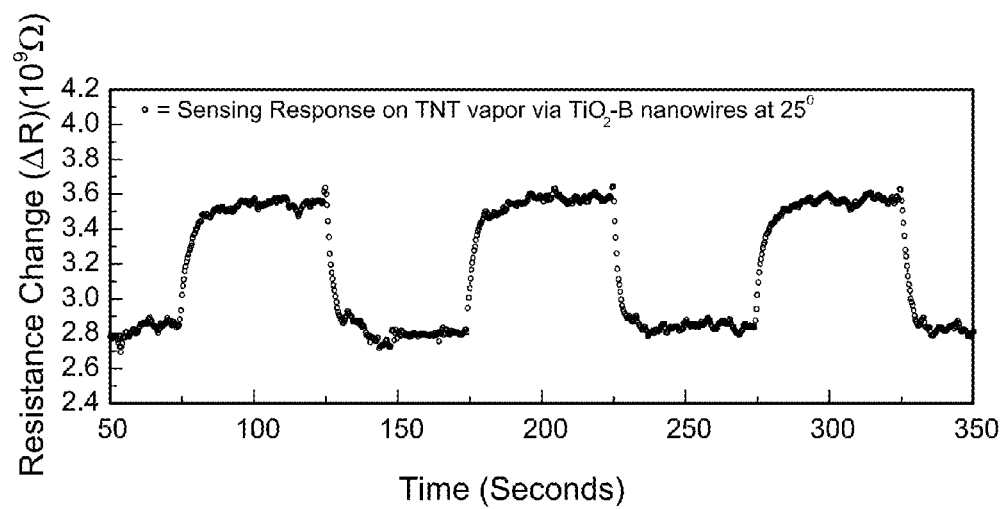
FIG. 5A is a graph of the resistance change of a representative device of the invention in response to TNT vapor.
Figure 5B:
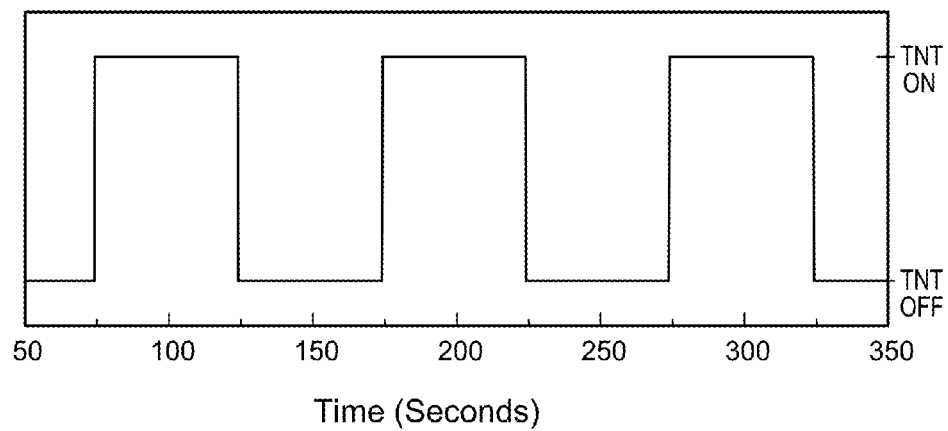
FIG. 5B is a graph representing the delivery signal of TNT vapor used to generate the data of FIG. 5A.
Figure 6A:
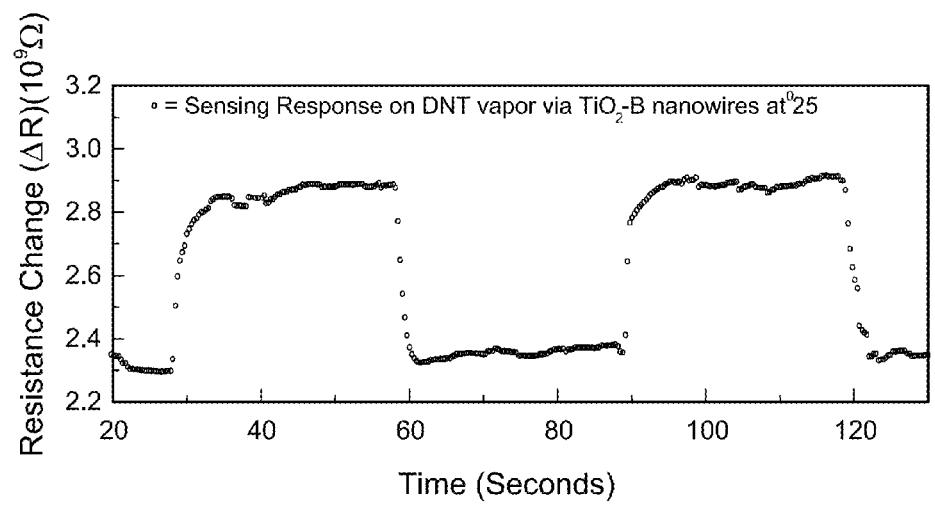
FIG. 6A is a graph of the resistance change of a representative device of the invention in response to dinitrotoluene (DNT) vapor.
Figure 6B:
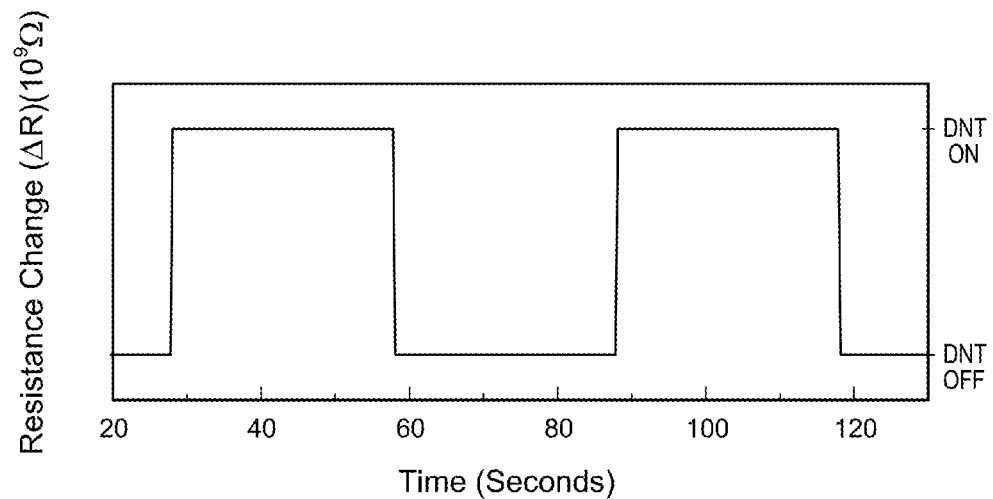
FIG. 6B is a graph representing the delivery signal of DNT vapor used to generate the data of FIG. 6A.

An exemplary representative device fabricated by the above-described method was utilized to test for the presence of analyte vapors of TNT and DNT. The devices included nanowires several hundred nanometers in diameter and about 2-3 microns in length. A typical response of a device to the analyte vapor is a 20-60% increase in resistance within one second of exposure to air that contains trace vapor of TNT or DNT. The response of a device to TNT is illustrated in FIG. 5A, with the related exposure timing for the TNT vapor illustrated in FIG. 5B. Similarly, the experimental data for the exposure of DNT to the device is illustrated in FIGS. 6A and 6B. As can be seen in FIGS. 5A and 6A, the detection time once the analyte is exposed to the device is less than 1 second, and the recovering time after the analyte vapor-filled air is replaced by fresh air is roughly 1 second, as well.

The terminal voltage of the resistance measurement for this exemplary embodiment is 1 volt.

Quantitative Analyte Measurement Using Devices of the Invention

Figure 7A:
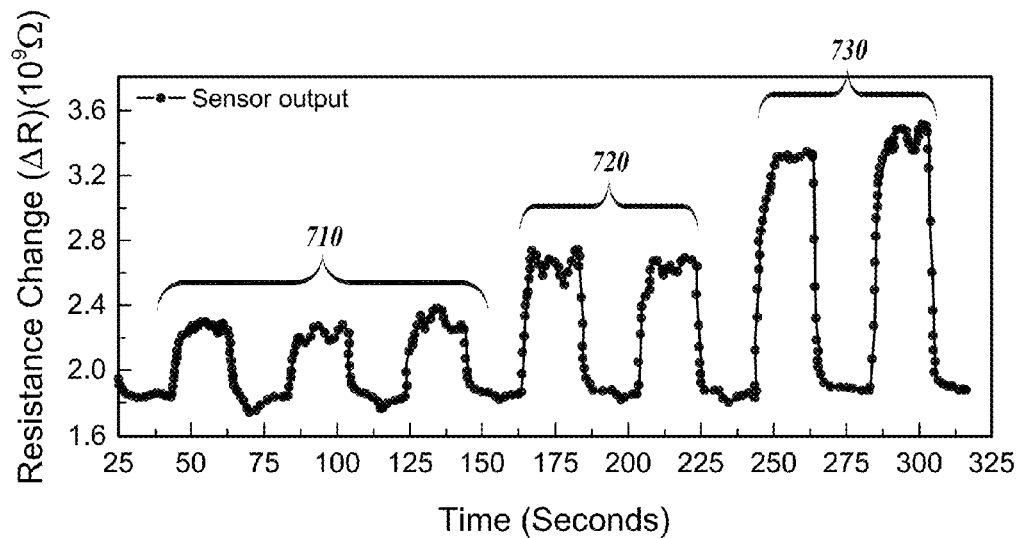
FIG. 7A is a graph of the resistance change of a representative device of the invention in response to DNT vapor at three different concentrations.
Figure 7B:
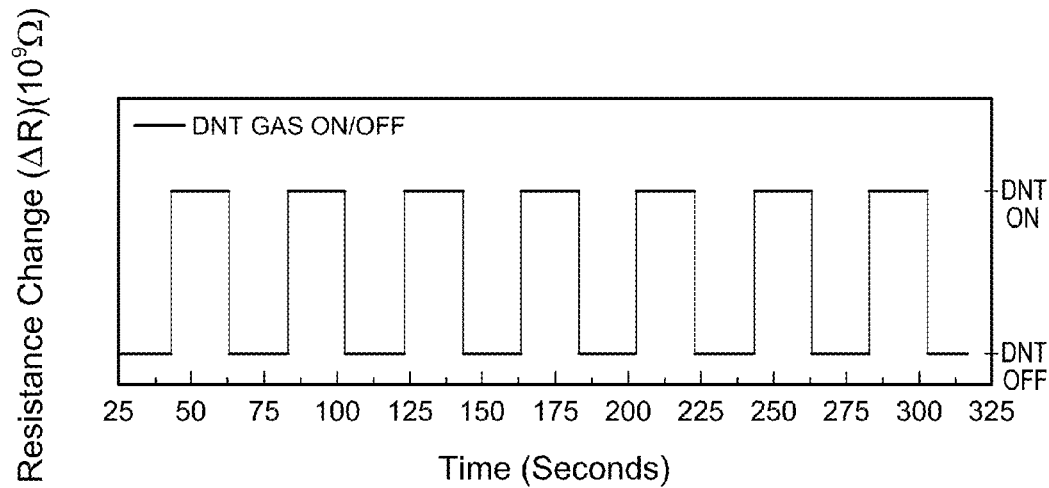
FIG. 7B is a graph representing the delivery signal of DNT vapor used to generate the data of FIG. 7A.

While the devices of the invention can be used as simple yes/no sensors for determining the presence of an analyte, the devices are also capable of quantitative characterization of a detected analyte at a part per billion (ppb) level or lower. Devices incorporating $TiO_2$—B films, as described above, were exposed to different levels of DNT to produce the data graphed in FIGS. 7A and 7B. Referring to FIG. 7A, the peaks 710 were acquired upon exposure of the device to 3 ppb DNT, peaks 720 were acquired with DNT at 5 ppb, and peaks 730 were acquired at 100 ppb DNT. Thus, the magnitude of resistance change of the device is indicative of the concentration of analytes detected by the device.

The Effect of Nanowire Length on Devices of the Invention

Figure 8:
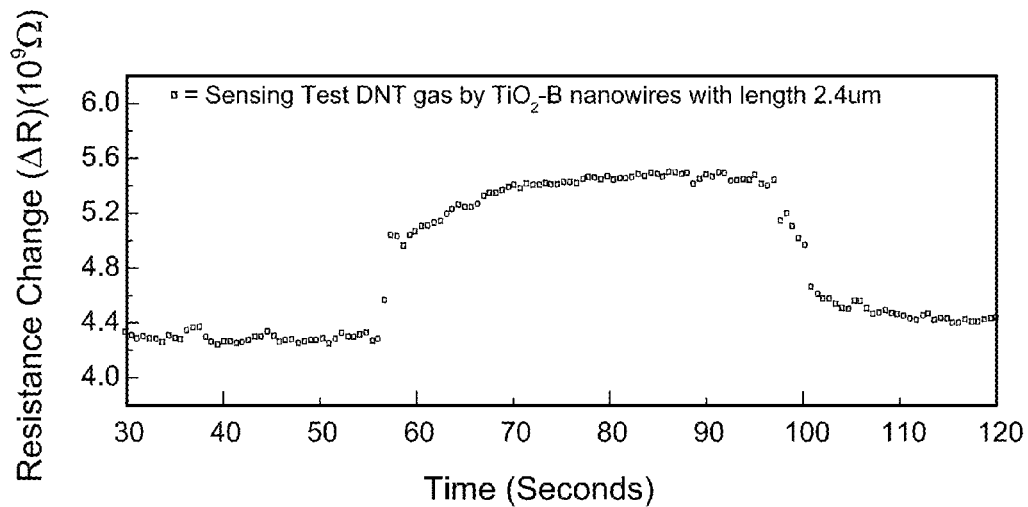
FIG. 8 is a graph of the resistance change of a representative device of the invention in response to DNT gas.
Figure 9:
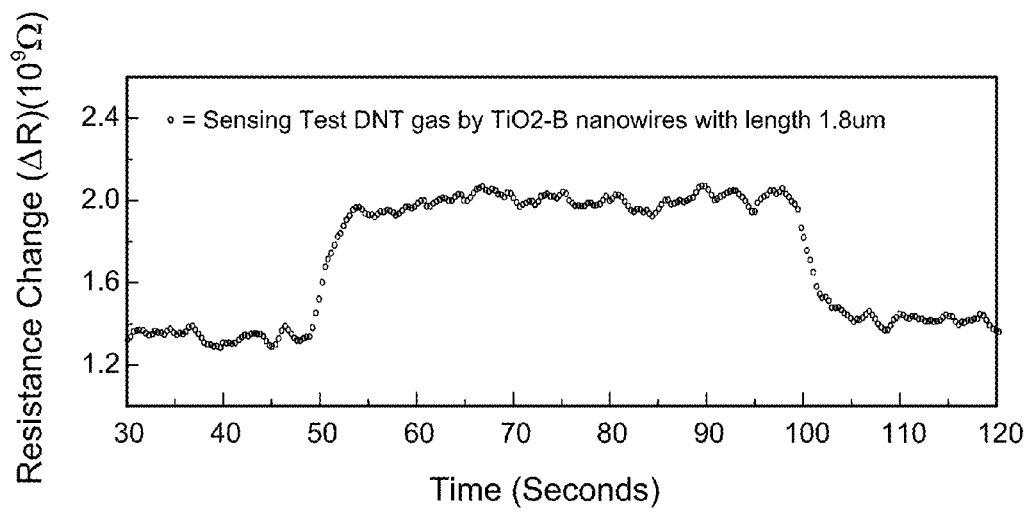
FIG. 9 is a graph of the resistance change of a representative device of the invention in response to DNT gas.

Devices similar to those described above including $TiO_2$—B nanostructured chemiresistive materials comprised of nanowires were modified such that the film of one device included nanowires with a length of about 2.4 micrometers and the film of a second device included nanowires with a length of about 1.8 micrometers. The experimental results are illustrated in FIG. 8 (2.4 micrometer nanowires) and FIG. 9 (1.8 micrometer nanowires). The length of the wires has no significant effect on the sensitivity of the devices; however, the shorter wires in FIG. 9 show a moderately slower response, with the device of FIG. 9 responding in about 1.06 seconds and the device of FIG. 8 responding in about 0.5 seconds. The denser packing leads to a slower permeation of vapor molecules into the film and, thus, the response is typically slower.

Because the distance between the two electrodes remains the same in the above device comparison, the mean path length is the same in these devices. However, the average number of junctions connecting different wires in the path is strongly dependent on the length of the wires. In the film made of shorter wires, charge carriers need to pass a larger number of junctions. The sensitivity is not affected by the number of junctions of the nanowires, as indicated by the experimental data because the charge transport in the individual nanowires is the primary factor contributing to the sensitivity of the devices. Thus, the length of nanowires does not affect the sensitivity but will affect the response time before detecting an analyte vapor.

Each individual analyte likely has an optimum length of nanowire that will produce the fastest response possible, contributed to partly by the size of the analyte molecule. For example, the response to TNT is slower than the response of a similar device to DNT (smaller than TNT) due to slower permeation of the larger TNT molecules.

The Effect of Nanowire Width on Devices of the Invention

While nanowire length does not significantly affect device sensitivity, as described above, the width of nanowires does. Thinner nanowires produce a larger response than thicker nanowires due to the increased susceptibility of thinner nanowires to the depletion of surface charges upon interaction with electronegative analyte molecules. Thus, thinner nanowires provide more sensitive devices. It will be appreciated that the sensitivity of a device to a particular analyte will be optimized based on an individual analyte, and no universal nanowire thickness provides the optimum sensitivity for every potential analyte.

Temperature Effect on Device Performance

Devices of the invention operate well at room temperature; whereas, devices known in the prior art typically operate at elevated temperatures (e.g., above 200° C.) based on an oxidation-reduction mechanism. Nanowires of semiconducting metal oxides have shown satisfactory performance for detecting gases, such as hydrogen and nitrogen dioxide at part per million (ppm) sensitivity levels. However, these gas sensors operate based on an oxidation-reduction reaction at an elevated temperature of over 200° C. Thus, while nanowires have been shown to be a viable material for detecting some gases, devices incorporating nanowires have the detrimental requirement of elevated temperatures for operation and a maximum sensitivity of parts per million.

Figure 10:
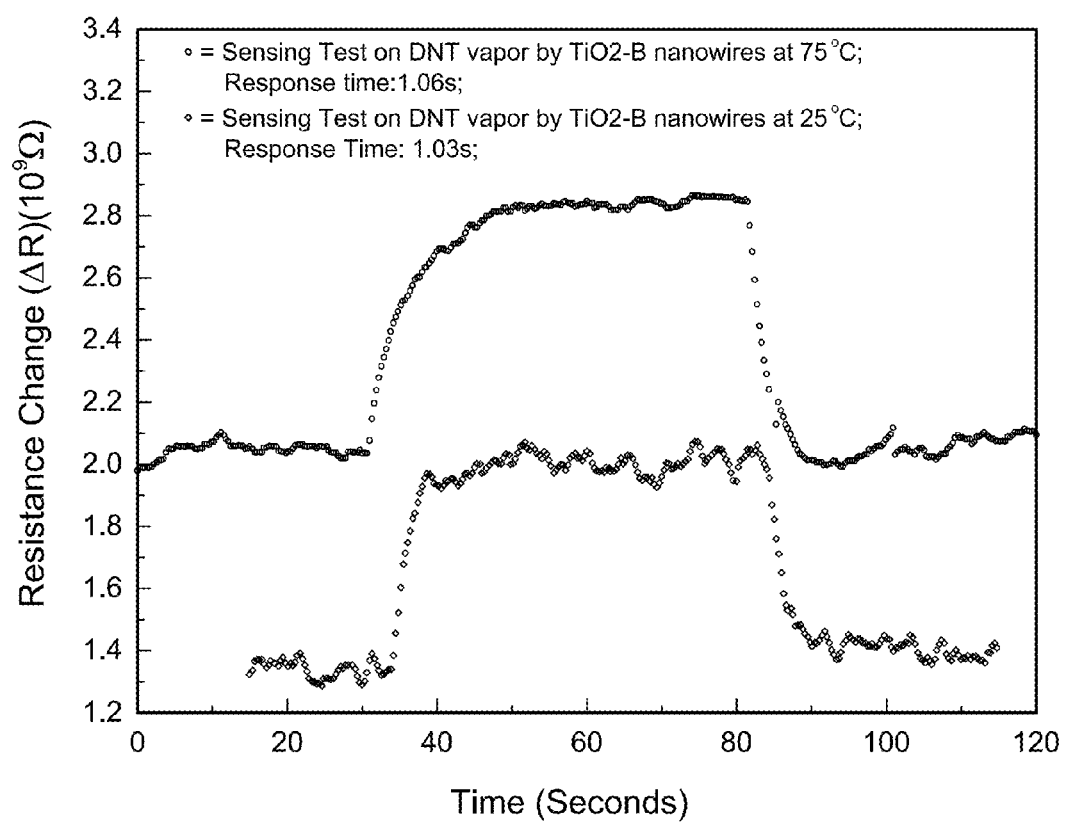
FIG. 10 is a graph of the resistance change of a representative device of the invention in response to DNT gas at two different temperatures.

The devices of the invention were tested at slightly elevated temperatures and at room temperature to determine the improvement, if any, resulting from elevated temperatures. The results are illustrated in FIG. 10, where it can be seen the sensitivity and response time of a device tested at 25° C. upon exposure to DNT and a device tested at 75° C. upon exposure to DNT are nearly identical. Thus, elevated temperatures do not significantly enhance the devices of the invention.

While illustrative embodiments have been illustrated and described, it will be appreciated that various changes can be made therein without departing from the spirit and scope of the invention.

The embodiments of the invention in which an exclusive property or privilege is claimed are defined as follows:

1. A device for detecting an electronegative analyte vapor, comprising:
   (a) a film comprising a nanostructured chemiresistive material having a first resistivity in the absence of an electronegative analyte vapor and a second resistivity, different than the first resistivity, after exposure to the electronegative analyte vapor, wherein the nanostructured chemiresistive material is a three-dimensional mesh that comprises a plurality of nanostructured materials selected from the group consisting of nanowires, nanotubes, nanoparticles, and mixtures thereof, and wherein the nanostructured chemiresistive material comprises monoclinic titanium dioxide; and
   (b) a resistivity-measuring device sized and configured to determine a resistivity of the film, wherein the resistivity measuring device comprises a first electrode and a second electrode on a surface of the film and spaced a distance apart from each other such that the first electrode is in resistive communication with the second electrode through a first sensing region of the film.

2. The device of claim 1, wherein the resistivity measuring device is sized and configured to electrically determine the resistivity between the first electrode and the second electrode through the first sensing region.

3. The device of claim 1, wherein the nanostructured chemiresistive material comprises monoclinic titanium dioxide nanowires.

4. The device of claim 1, wherein the nanostructured chemiresistive material further comprises gold nanoparticles.

5. The device of claim 1, wherein the nanostructured chemiresistive material comprises a functionalized surface.

6. The device of claim 1, wherein the nanostructured chemiresistive material comprises a first nanostructured chemiresistive material and a second nanostructured chemiresistive material.

7. The device of claim 6, wherein the resistivity measuring device is sized and configured to measure the resistivity of the first nanostructured chemiresistive material and the second nanostructured chemiresistive material separately.

8. The device of claim 1, wherein the difference between the first resistivity and the second resistivity results from the formation of a charge carrier depletion region at an interface between the nanostructured chemiresistive material and the electronegative analyte vapor.

9. The device of claim 1, wherein the first resistivity is less than the second resistivity.

10. The device of claim 1, wherein the electronegative analyte vapor is a nitroaromatic compound vapor.

11. The device of claim 1, wherein the electronegative analyte vapor is a vapor of a compound selected from the group consisting of trinitrotoluene, dinitrotoluene, cyclotetramethylenetetranitramine, cyclotrimethylenetrinitramine, 2,4,6-trinitrophenol, methyl-2,4,6-trinitrophenylnitramine, pentaerythritol-tetranitrate, silicon-pentaerythritol-tetranitrate, nitroglycerine, and mixtures thereof.

12. The device of claim 2, further comprising:
   a third electrode in contact with the film, a fourth electrode in contact with the film, and a second sensing region of the film intermediate the third electrode and the fourth electrode, such that the third electrode is in resistive communication with the fourth electrode through the second sensing region, wherein the second sensing region comprises a plurality of nanostructured materials in between the third electrode and the fourth electrode;
   wherein the resistivity-measuring device is sized and configured to electrically determine the resistivity between the third electrode and the fourth electrode through the second sensing region for comparison to the determined resistivity in the first sensing region; and
   wherein the first electrode and the second electrode are spaced a first distance apart from each other on the film, wherein the third electrode and the fourth electrode are spaced a second distance apart from each other on the film, and wherein the first distance and the second distance are different.

* * * * *

UNITED STATES PATENT AND TRADEMARK OFFICE
CERTIFICATE OF CORRECTION

PATENT NO. : 8,673,216 B2  
APPLICATION NO. : 12/960341  
DATED : March 18, 2014  
INVENTOR(S) : A. Chen et al.

Page 1 of 1

It is certified that error appears in the above-identified patent and that said Letters Patent is hereby corrected as shown below:

In the Claims

| COLUMN | LINE | ERROR |
|---|---|---|
| 10 | 40 | "methyl-2,4,6-trinitrophenyInitramine" should read |
| (Claim 11, | line 5) | --methyl-2,4,6-trinitrophenylnitramine-- |

Signed and Sealed this
Twelfth Day of August, 2014

Michelle K. Lee
*Deputy Director of the United States Patent and Trademark Office*